United States Patent [19]

Mignard

[11] 4,245,627

[45] Jan. 20, 1981

[54] ORTHOPAEDIC APPARATUS FOR SPINAL TREATMENT

[76] Inventor: Jean Mignard, 75, rue de la Plage, 62600 Berck-Plage, France

[21] Appl. No.: 41,659

[22] Filed: May 23, 1979

[30] Foreign Application Priority Data

| Apr. 30, 1976 | [FR] | France | 76 13210 |
| May 23, 1978 | [FR] | France | 78 15496 |
| Mar. 23, 1979 | [FR] | France | 79 07735 |

[51] Int. Cl.³ .................................................. A61H 1/02
[52] U.S. Cl. ......................................... 128/78; 128/75
[58] Field of Search ............... 128/78, 68, 75, 87 B, 128/87 R, 88, 89 R

[56] References Cited

U.S. PATENT DOCUMENTS

| 1,935,859 | 11/1933 | Putz | 128/78 |
| 3,094,984 | 6/1963 | Jewett | 128/78 |
| 3,771,513 | 11/1973 | Velazquez | 128/87 B |
| 3,938,509 | 2/1976 | Barber | 128/89 R |

FOREIGN PATENT DOCUMENTS

| 66387 | 12/1891 | Fed. Rep. of Germany | 128/78 |
| 2502202 | 7/1975 | Fed. Rep. of Germany | 128/78 |
| 1276078 | 10/1961 | France | 128/75 |
| 2031200 | 11/1970 | France | 128/75 |
| 2349321 | 11/1977 | France | 128/75 |
| 720282 | 12/1954 | United Kingdom | 128/78 |

Primary Examiner—Robert W. Michell
Assistant Examiner—Arthur S. Rose
Attorney, Agent, or Firm—Karl W. Flocks

[57] ABSTRACT

This invention relates to an orthopaedic apparatus for treatment of the spine.

The apparatus is comprised of a pelvic girdle being supported on at least one trochanter, an abdominal plate and two lateral shells fixed directly onto the patient by all methods.

This device, which can be completed by stiff rods and a system of removable neck and head braces, enables the spinal column to be corrected in the desired direction while leaving the patient great freedom of movement.

15 Claims, 23 Drawing Figures

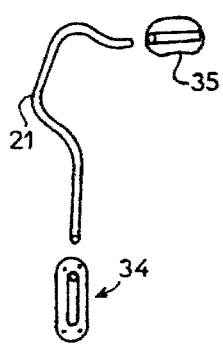
FIG. 9
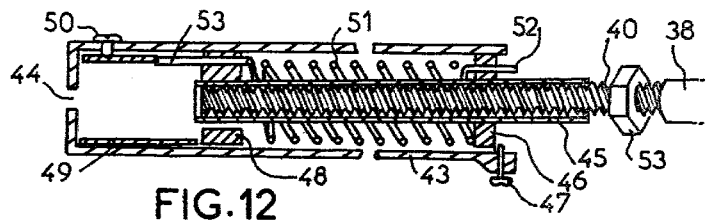
FIG. 12
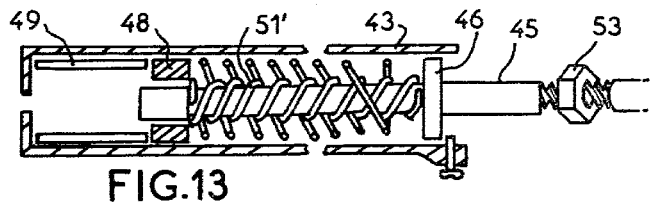
FIG. 13
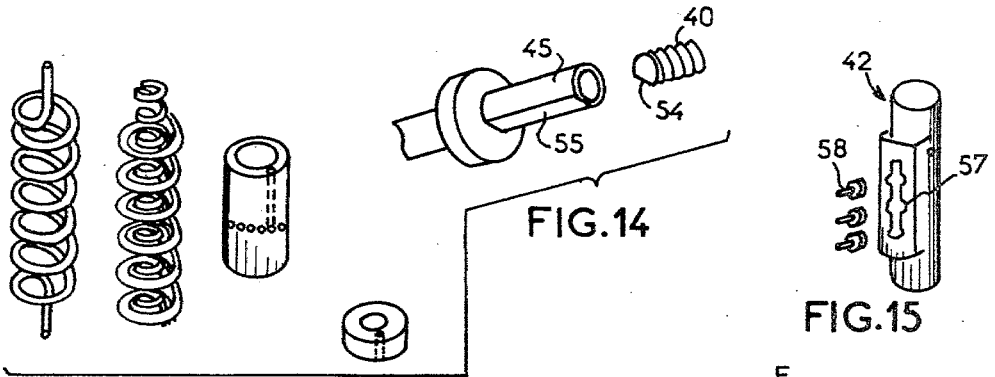
FIG. 14
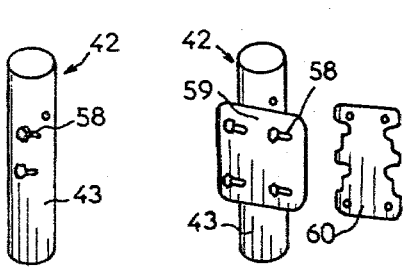
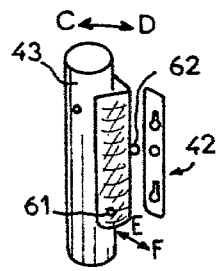
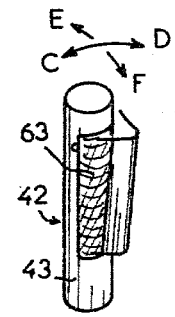
FIG. 15
FIG. 16  FIG. 17  FIG. 18  FIG. 19
FIG. 20  FIG. 21  FIG. 22  FIG. 23
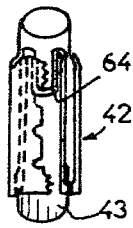
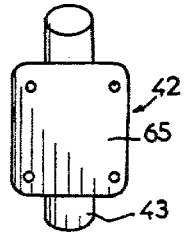
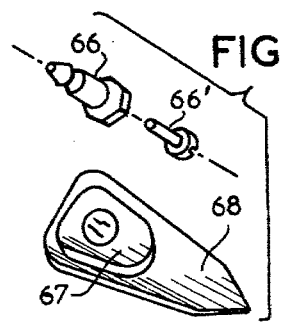
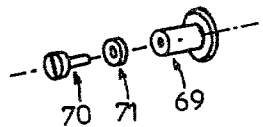

ORTHOPAEDIC APPARATUS FOR SPINAL TREATMENT

The invention in question relates to an orthopaedic apparatus designed to rectify spinal deformations such as lateral curvature, kyphosis, hyperlordosis, etc.

Until now, patients with these deformations were fitted with corsets which were either made in one piece to maintain the trunk in a given position by gripping the rib cage or else were made up of adjustable vertical components bearing cross iron pieces forming numerous rigid supports. These corsets, generally put on patients after plaster treatment, allow only of passive correction. Even when a stiff spinal brace or a strap traction system is associated with them, there is a notable decline in rectification as obtained by the use of plaster. Moreover, they need a lot of room under clothing and they lack elasticity in the brace support layout: yet again, these corsets grip the human trunk intensely, which is harmful to its mobility, particularly in lateral and forward and backward movements.

The invention under reference eliminates these drawbacks.

It consists of an orthopaedic apparatus for treatment of the spine which is distinguished by the fact that it combines the following components:

a rigid pelvic girdle encompassing the pelvis, being supported by at least one of the trochanters, with a raised rear section forming a rest back and with two fore tips spaced between each other so as to provide a central opening, an abdominal stiff plate, generally trapezoidal or V-shaped with rounded corners with its large base upwards and its small base downwards, with the lower extremity fixed under the anterior tips of the pelvic girdle, its upper part having a concave side turned towards the patient's stomach and whose upper extremity ends at the level of the xyphoid appendix, and two rigid lateral shells, each being of a general U shape, chanelled in the middle at top and bottom to fit to the shape of one of the patient's ribs by overlapping the hip crest, and of which the respective forward parts, with a height which is practically identical and lower than that of the abdominal plate, are both secured on the median or upper part of the abdominal plate, or on both parts at the same time, and whose rear parts, which are considerably higher than their respective fore parts, are both fixed onto the rear raised part, forming a back rest for the pelvic girdle.

This kind of structure makes it easier to place the apparatus by assembling the various constituent components directly on the patient: it gives a better way of adapting these components to each individual morphology, and allows of gradual adjustment of the desired rectification(s), by relative displacement of various components in relation to each other: lastly, braces of known varieties can be adapted to cause elongation of the spinal column.

The invention in question will be described in detail using the following drawings, in which.

Figure 5:
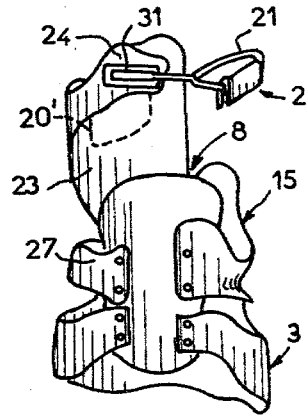
Figure 6:
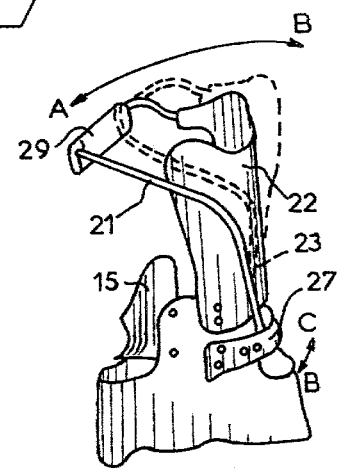
Figure 7:
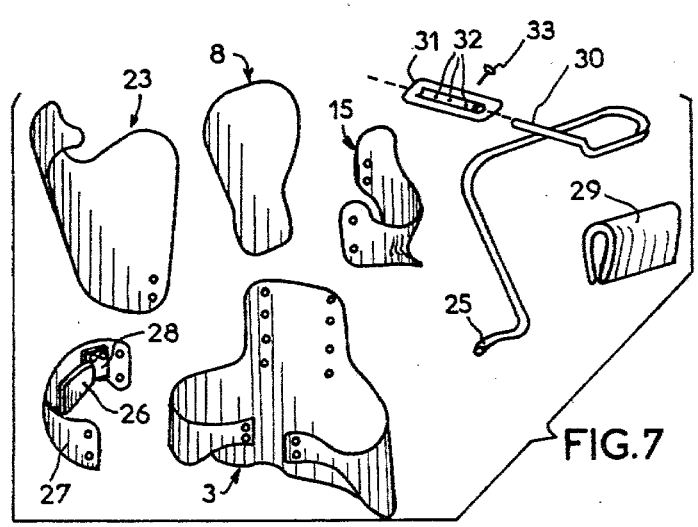
Figure 8:
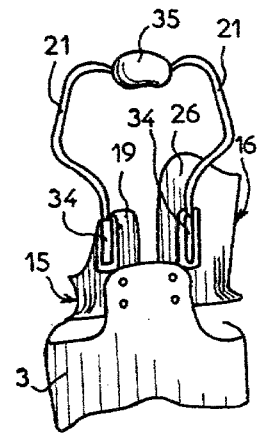
Figure 10:
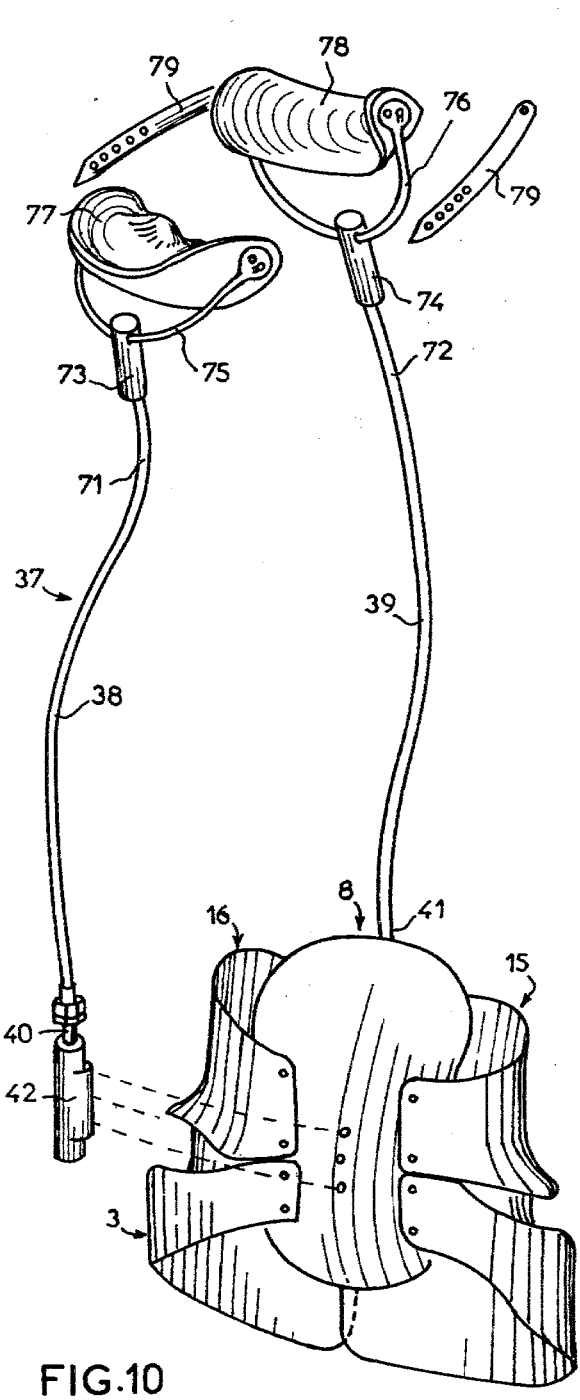
Figure 11:
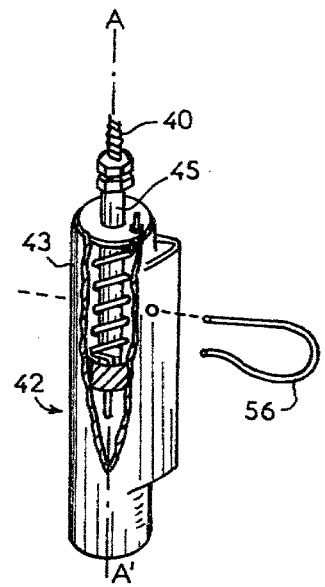

FIGS. 5 and 6 show a variation of the invention seen respectively from front and rear, FIG. 7 is an exploded view of the apparatus components as shown on FIGS. 5 and 6, FIG. 8 is another alternative of the invention and FIG. 9 shows the components thereof, FIG. 10 shows the apparatus as per the invention with a brace added, FIGS. 11 and 12 depict respectively a partial cut-out view and a section as per line A—A' of FIG. 11, of the brace support layout, on an enlarged scale, FIG. 13 shows an alternative solution for such a support layout, FIG. 14 illustrates various constructional details of these support layouts, FIGS. 15 to 21 depict various methods of fixing brace supports to the invention when adapted to the apparatus, and FIGS. 22 and 23 show examples of fixation methods for various components of the apparatus between themselves when adapted to the invention.

Figure 1:
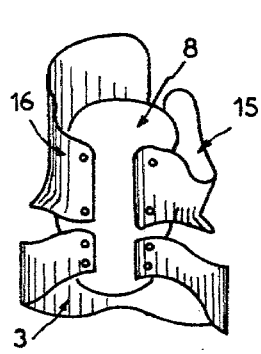
FIG. 1 shows a first preferable execution of the apparatus seen from the front.
Figure 2:
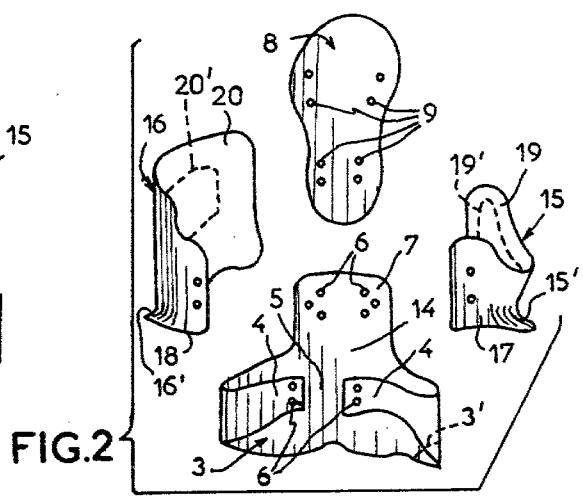
FIG. 2 is an exploded view of various components for executing FIG. 1.
Figure 3:
FIG. 3 is a section view of the abdominal plate shown on FIGS. 1 and 2, and showing a S-shaped profile.
Figure 4:
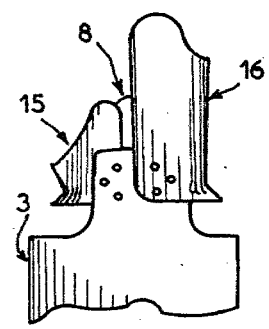
FIG. 4 is a rear view of execution of FIGS. 1 and 2.

Pelvic girdle 3 is, for the invention, the basic element: it consists, as demonstrated in FIGS. 1 and 2 of a rigid component 3, generally of circular shape, which encompasses the pelvis, moulding itself to the buttocks and is supported by at least one of the trochanters to finish by two fore extremities 4 separated from each other so as to provide the opening 5.

This opening can enable the patient to pull on the belt when it is made in one piece. The belt may however be formed of two rigid lateral elements linked together along a vertical line located opposite opening 5 to enable the person being fitted with the apparatus to slip on the belt either from the front by opening 5, or from behind, where the two elements mounted crosswise are then linked together along the vertical line, by overlap.

The rear central part 14 of the belt and its two anterior tips 4 are fitted with one or several sets of perforations 6, which can accommodate all known fixation methods, especially of the groove lug type with push-buttons or screw-lugs as respectively shown on FIGS. 22 and 23 to secure the other components of the apparatus according to the invention.

The belt, which is shaped like a ring not closed in front, should preferentially show a rear raised central part 7 forming a back-rest, which serves to fix the other elements of the apparatus, namely the lumbar and dorsal lateral shells.

The abdominal plate 8 acts as a link piece for the different components making up the apparatus as per the invention: it consists of a rigid element, generally V-shaped with rounded corners which, as is particularly shown in FIGS. 1 and 10, is covered over by the fore extremities 4 of the pelvic girdle 3 on its lower part: its upper part shows a concave side turned towards the patient's stomach and it finishes at the level of the xyphoid appendix to free the patients rib cage.

This plate has one or several sets of perforation holes 9 in its lower part to enable it to be secured to pelvic girdle 3 and for its upper part to be attached by standard methods to lateral shells.

According to the invention the apparatus has two transversal shells 15 and 16 which cover the patient's flanks, and each of them is formed of a rigid general shape of a U, with notches at top and bottom to fit one of the patient's sides by straddling the hip bone crest, the lower part having a 15' or 16' rim varying in prominence to rest on the hip bone crest.

These two shells each have a forward part 17, 18 and a hind part 19, 20 which are fixed respectively to the upper part of the abdominal plate 8 and to the central rear part of the pelvic girdle 3 and particularly on the raised part of the latter which forms the back.

The height of the forward part 17, 18 of each of the two shells 15, 16 is roughly the same and less than the top of the abdominal plate 8, when these different elements are fitted on the patient, but the height of their rear parts 19, 20 is appreciably higher than that of their respetive forward parts.

Thus, one of the shells 15 can bear the patient's spinal flexure corresponding to lumbar vertebrae whilst the other shell 16 has a rear part which extends to the dorsal vertebrae, as depicted on FIGS. 1 and 5 to correct the dorsal curve of the spine or to act as counter-bracing to the lumbar shell 15;

In another version as shown in FIG. 10, the two shells 15, 16 may be of identical dimensions, for treatment of hyperlordosis or kyphosis.

The various components of the apparatus can be made in any material at all provided it is sufficiently rigid to obtain the corrections under consideration, such as plastic material, metal or natural matter. They are more or less thick according to the degree of rigidity and the greater or lesser pressure to be exerted on one or several specific points of the patient's body.

Preferred raw materials for manufacture of the apparatus' different components according to the invention are plastic materials, and particularly those selected from the group comprised by polyethylene, polypropylene, nylon, and methyl acrylonitrile-polymethacrylate copolymer.

They are utilized in the form of plates, generally with an inclusive thickness of 2 to 5 mm, and preferably between 3 and 4 mm, which are cut out and shaped in function of the patient's morphology and in forms which give flexible parts.

Provision can also be made for support or strengthening parts, particularly in closed cell foam, with a suitable shape, quality and thickness, which are placed in carefully selected spots to strengthen the corrective action of the various components of the apparatus.

Thus it is that provision can be made for such a part in 3' on the trochanter support of the pelvic girdle, depicted on FIG. 2 in dotted lines: another supporting 19' part, generally triangular in shape, can be arranged on the lumbar shell 15 with a vertical side which repels the spinal curvature to be corrected: lastly, another support part of 20', for example quadrangular in shape, can be placed inside the shell 16 (FIG. 2) or in a component of the latter 23 (FIG. 5) to strengthen support on a dorsal hump.

According to the invention, all the components, that is to say the pelvic girdle, the abdominal plate and the two lateral shells, once they are placed in position, work together to bring about rachis erection with the necessary lateral pressures to exercise spinal column corrections according to clinical cases.

The apparatus can also carry a certain number of additional components, such as metal rods to act on gibbosities and rectify the spinal column, or an occipito-mental device to cause continual or intermittent spine elongation.

It is in fact possible to provide for addition of one or several metal rods or steel bars 21 or in any other material with similar resistance, tensile strength and elastic qualities, whose ends rest on cradles made in the parts of two different components of the apparatus on the same side of the patient's body, the rod being supported between its two tips on the opposite side of the patient.

For example, as shown on FIGS. 5 and 6, a metal rod 21 can be horizontally supported on the right hand side of the pelvic girdle, rise almost vertically to the height of a gibbosity to be corrected by bearing on the rear part 22 of a dorsal shell located on the right side, cross the back diagonally, go under the left armpit and finish almost horizontally on a raised forward extension 24 of this dorsal shell.

In this version, the dorsal shell is composed of two elements 23 and 27, the lower component 27 comprising, as depicted on FIG. 7, a cradle 26, situated towards the interior, which takes the lower extremity of metal rod 21. This rod extremity 21 is wedged in cradle 26 by a key 28, to regulate rotation of the upper part of the trunk in the direction CB (FIG. 6).

A floating protective device 29, located on the rod at the place where it is in contact with the body under the armpit is shown on FIG. 7. The other end of the rod 30 is pierced and passes through a cradle 31 in the form of a tubular slide fitted with perforations 32 and arranged on forward extension 24 of element 23 of the right hand dorsal shell. Pin 33, which positions the perforations of the rod and the slide to face each other, enables adjustment to be effected in function of the patient's morphology. It should be noted that this sort of layout allows the patient to bend down laterally both to right and left (Arrow AB), by acting through support on the hump with derotation.

In another version depicted on FIG. 8, the first metal rod or bar 21 starts from a vertical housing 34, also in the form of a tubular slide located in the foward part 19 of one of the lateral shells 15, where its tip is simply threated, passes under the corresponding armpit and then in front of the rib cage where it terminates on a sternal support 35; similarly another metal rod 21 starts from the same sternal support 35, goes under the other armpit and finishes in a similar vertical housing 34 located in the forward part 26 of the other shell 16.

The occipito-mental or brace device which can be adapted to the apparatus according to the invention can be of an already known type such as those described in French letters Pat. Nos. 1.276.078, 2.031.200 or 2.349.321, or else like those utilized in Milwaukee devices, or a new kind which will now be described in detail and which presents the advantage over the previous ones of combining a very simple form of structure with a greater freedom of movement for the patient.

The brace designated by general reference number 37 is essentially made up of two vertical rising rods 38, 39 arranged according to the patient's plane of symmetry, threaded at least on their lower ends 40, 41 where they are inserted into a support device 42 fastened to one of the apparatus components according to the invention, and whose upper ends 71, 72 are linked respectively by means of a collar 73, 74 and a cradle 75, 76 to a chin bandage support 77 and to a headstall 78 linked together by straps 79.

A special version of support layout 42 of the threaded lower end of each upright rod is shown in detail on FIGS. 11 and 12. This layout 42 is comprised of a cylinder 43 solid with a U-shaped base with standard methods of fixation on one component of the apparatus according to the invention, for example onto pelvic girdle 3 and abdominal plate 8.

This cylinder 43, generally closed on its lower part or with a threaded hole 44, receives the tube 45 fitted with a flange 46. This tube 45, held inside cylinder 43 by a blocking method such as screw 47, slides in a guide bush 48 freely resting on a travel band 49 fixed in an adjustable way onto cylinder wall 43 by the screw 50. A compression and torsion spring 51, whose end 53 is attached to guide bush 48, permanently attracts tube 45 to its open upper end by causing flange 46 to strike against blocking screw 47.

The threaded tip 40 (or 41) of the rising rod 38 (or 39) is fitted with a device which prevents it from rotating in tube 45, such as the flatted end 54 and it is threaded into tube 45, which has a corresponding flatted end 55.

Rod 38, like rod 39, rests on the tube extremity through one or several nuts 53 of which the setting on the threaded part 40 (or 41) of the rod can be regulated.

Spring 51 can also have another spring 51' added to it, wrapped around the first opening spring with an opposite thread to obtain a more active thrust (see FIG. 13).

A clamped clip 56, removable, can be inserted transversally in the cylinder 43 to be able contingently to execute intermittent treatment.

This kind of telescopic support for the brace allows the traction and rotation exercised on the spine to be regulated, whilst leaving the patient maximum freedom and yet keeping up a progessive effect.

It is in fact important to avoid any effect of too prolonged lengthwise traction or of too advanced torsion which could cause the patient to have dental problems.

This is why provision has been made to control spring travel in both the vertical thrust and rotating directions. P These supporting devices 42 of brace 37 are attached to abdominal plate 8 and to the raised rear portion forming the back 7 of the pelvic girdle, using all the methods, especially those shown on FIGS. 15 to 21.

FIG. 15 depicts a detachable system of fixing supports 42 by a slotted slide 57 fitted out in a U-shaped ring and able to receive studs 58: FIG. 16 shows the reverse case where studs are solid with cylinder 43; FIG. 17 depicts a plate 59 solid with cylinder 43 and fitted with studs 58 which can be attached on to apparatus components which are equipped with the corresponding hooking on parts, such as slide 60.

Following the version illustrated by FIG. 18, the method for attaching and releasing, movable in itself, the brace support device, is comprised of a pivot arrangement allowing of rotations according to a first horizontal axis 61 and a second horizontal axis 62 which is perpendicular to the first and situated in the patients plane of symmetry: such a system allows of bending in the two perpendicular directions CD and EF.

The same result can be obtained by sinking the cylinder 43 in an elastic mass 63 as shown on FIG. 19.

FIG. 20 shows how these different methods of attachment can include a removable spring 64 enabling devices 42 to be blocked in their attachment position.

FIG. 21 shows a cylinder 43 solid with a plate 65 fitted with single perforations to pass through it fixing methods of the same type as those used to fix together the various components of the apparatus according to the invention.

Such fixing methods include, for example, groove lugs fixed by a 66' screw, on which can be threaded a press-stud 67 fixed on a spline 68 (FIG. 22) and/or a system 69 of screw lugs 70 and washers 71 (FIG. 23).

I claim:

1. An orthopaedic apparatus for treatment of the spinal column, distinguished by the fact that it is comprised of the following components:
   a rigid pelvic girdle shaped such that it may be wrapped around the pelvis and supported by at least one of the trochanters, with a raised rear part forming the back and with two forward extremities interspaced between them so as to form a central opening,
   a rigid abdominal plate, generally V-shaped with rounded off corners, having its large base at the top and its small base at the bottom, whose lower end is affixed under the forward extremities of the pelvic girdle, and has in its upper part a concavity positioned such that when the apparatus is worn said concavity will be turned towards the patient's stomach, with the upper extremity finishing at the height of the xyphoid appendix; and
   two rigid lateral shells, each generally U-shaped and notched in the middle at top and bottom to fit one side of the patient by straddling the hip bone crest, their lower part forming a rim to be supported on the hip bone crest and with the respective forward parts of almost identical height and lower than that of the abdominal plate, both being fixed on the middle or upper part of the abdominal plate, with rear parts with a height appreciably greater than that of their respective forward parts, both fixed onto the raised rear part which forms the back of the pelvic girdle.

2. Apparatus according to claim 1, distinguished in that the pelvic girdle consists of two rigid lateral components linked together along a vertical line situated in the vicinity of the axis of the raised part forming the back.

3. Apparatus according to claim 1, distinguished by the fact that the rear parts of the two lateral shells are of identical height.

4. Apparatus as per claim 1, characterized by the fact that the rear parts of the two lateral shells vary in height, one being raised to go only along lumbar vertebrae and the other rising to the height of dorsal vertebrae.

5. Apparatus as per claim 4, characterized by the fact that one of the rigid lateral shells is composed of two parts, with the lower part having a cradle towards the inside of the apparatus.

6. Apparatus as per claim 1, characterized by the fact that it also includes a rigid metal rod with one tip resting on a cradle fixed to a part of a first component of the apparatus and the other tip on a cradle fixed to a part of a second component of the apparatus, this rod being supported between its two ends on that part of the patient's body which is opposite that on which is situated the said parts of the first and second components.

7. Apparatus as per claim 6, characterized by the fact that the rigid metal rod is adapted to be supported on a gibbosity of the body.

8. Apparatus as per claim 6, characterized by the fact that the cradle taking the tip of the rigid metal rod takes the form of a tubular slide.

9. Apparatus as per claim 1, characterized by the fact that one or several of the apparatus' components comprise support or strengthening parts in closed cell foam, designed to strengthen the corrective action of the said components on the spine.

10. Apparatus as per claim 1, characterized by the fact that the means of fixing together the various parts of the apparatus consist of studs, whose outer diameter corresponds to the inner diameter of perforations provided for in various parts of the apparatus.

11. Apparatus as per claim 1, characterized by the fact that it also includes occipito-mental support points located on the apparatus.

12. Apparatus as per claim 11, characterized by the fact that the occipito-mental support is comprised of two vertical threaded upright rods adapted to be situated in the patient's plane of symmetry and whose upper tip is linked respectively by a ring and a cradle to a chin bandage support and to a headstall and whose lower ends each rest, thanks to one or several height adustment screws, in a telescopic device fixed to the pelvic girdle.

13. Apparatus as per claim 12, characterized by the fact that each telescopic device comprises a hollow tube to receive the end of a threaded upright rod and equipped with a flange and a travel ring between which is inserted at least one spring and a guide bush, the tube and the two bushes being laid out inside a cylinder which is solid with a plate fixed to the pelvic girdle.

14. Apparatus as per claim 13, characterized by the fact that each cylinder of the telescopic devices is fixed to the girdle by an attachment system comprising a pivot pin allowing the cylinder to revolve around two perpendicular horizontal axes of which one is located when the apparatus is worn in the patient's plane of symmetry.

15. Apparatus as per claim 13, characterized by the fact that the tips of the telescopic device spring are made solid respectively with the flange and the cylinder and that the tip of the threaded upright rod and that of the tube receiving the latter are both fitted with a method preventing the rod from rotating in relation to the tube.

* * * * *

UNITED STATES PATENT AND TRADEMARK OFFICE
CERTIFICATE OF CORRECTION

PATENT NO. : 4,245,627
DATED : Jan. 20, 1981
INVENTOR(S) : Jean MIGNARD

It is certified that error appears in the above—identified patent and that said Letters Patent is hereby corrected as shown below:

Title Page [30] Foreign Application Priority Data should read as follows:

[30] Foreign Application Priority Data

May 23, 1978 [FR] France .............. 78 15496
Mar. 23, 1979 [FR] France .............. 79 07735

Signed and Sealed this

Fourth Day of August 1981

[SEAL]

Attest:

GERALD J. MOSSINGHOFF

Attesting Officer     Commissioner of Patents and Trademarks